United States Patent
Catlin, Jr.

(10) Patent No.: US 11,175,270 B2
(45) Date of Patent: Nov. 16, 2021

(54) HOME AND BUSINESS MONITORING SYSTEM AND METHODS

(71) Applicant: William H Catlin, Jr., Wayland, MA (US)

(72) Inventor: William H Catlin, Jr., Wayland, MA (US)

(73) Assignee: SenseSafe, LLC, Boston, MA (US)

( * ) Notice: Subject to any disclaimer, the term of this patent is extended or adjusted under 35 U.S.C. 154(b) by 283 days.

(21) Appl. No.: 16/391,123

(22) Filed: Apr. 22, 2019

(65) Prior Publication Data
US 2019/0324006 A1   Oct. 24, 2019

Related U.S. Application Data

(60) Provisional application No. 62/661,116, filed on Apr. 23, 2018.

(51) Int. Cl.
| | | |
|---|---|---|
| G01N 31/00 | (2006.01) |
| G01N 33/00 | (2006.01) |
| H04L 12/28 | (2006.01) |
| G01D 4/00 | (2006.01) |

(52) U.S. Cl.
CPC ........ *G01N 33/0063* (2013.01); *G01D 4/006* (2013.01); *H04L 12/2818* (2013.01); *H04L 12/2825* (2013.01)

(58) Field of Classification Search
None
See application file for complete search history.

(56) References Cited

U.S. PATENT DOCUMENTS

| | | | |
|---|---|---|---|
| 2011/0050395 A1* | 3/2011 | Ervin | G01M 3/26 340/6.11 |
| 2013/0340500 A1* | 12/2013 | Miller | G01N 25/56 73/29.02 |
| 2017/0344044 A1* | 11/2017 | Imes | G05D 23/00 |
| 2018/0004176 A1* | 1/2018 | Tsubota | H04L 12/2818 |
| 2018/0158315 A1* | 6/2018 | Sloo | G08B 17/117 |
| 2018/0198841 A1* | 7/2018 | Chmielewski | H04L 12/2818 |

FOREIGN PATENT DOCUMENTS

| | | | | |
|---|---|---|---|---|
| WO | WO-2012092622 A2 * | 7/2012 | | G05D 23/1919 |
| WO | WO-2014015370 A1 * | 1/2014 | | G06Q 50/06 |
| WO | WO-2016179315 A1 * | 11/2016 | | F24F 11/30 |

* cited by examiner

*Primary Examiner* — Phyllis A Book

(57) ABSTRACT

The systems of the present invention provide monitoring and recording means for monitoring and maintaining a history of one or more parameters associated with a building or a particular location. The system can be preset with default actions to be conducted as a result of certain events or changes in certain parameters being detected. For example, the water and/or gas utilities can be programmed to shut down if smoke is detected, indicating the possible presence of a fire, or if the temperature drops below freezing temperature. All utilities, including gas, and water can be programmed to shut down in the event that a potentially significant change in a monitored parameter is detected.

8 Claims, 6 Drawing Sheets

Power & Circuit Components

110 Power Supply

Control Module

Battery Backup

Power Cord

Optional Functionality

Disable
- Water
  - Battery Backup
  - Power goes out - water turns off
  - Seismic activity - water turns off
  - House unoccupied - water turns off
- Gas
  - Seismic activity - gas turns off/Notify
  - Senses a leak – gas turns off/Notify
- Oil
  - Senses a leak – turns off/Notify
- Washing Machine Hookup – Auto turn off

HOME AND BUSINESS MONITORING SYSTEM AND METHODS

SenseSafe™ (formerly MonitorSafe™) is a stand-alone device that can be placed on site, for example, in the basement or utility room of a residence, commercial, industrial, multifamily or other building and plugs into a standard electrical outlet. SenseSafe, once plugged in, tracks specific events and reports in real-time to an application (App) and website, as well as storing historical data for future reference. Recent improvements in integral systems utilizing wireless connections with the world-wide net have made remote monitoring, interaction and control of conditions, utilities, and other parameters existing at residential, commercial, industrial or other sites.

Existing systems that are offered have limitations in their functionality and connectivity.

WallyHome sensor system is intended to detect changes in moisture, temperature and humidity in the home. See http://www.sears.com/wallyhome-starter-kit/p-05743165000P, accessed Apr. 8, 2018

The Nest® system provides the ability to remotely monitor and control a number of conditions and utilities, such as smoke and carbon monoxide detection. The conditions and utilities can be monitored, for example, using an app that can be downloaded to the users' cell phone and used remotely. See https://nest.com/smoke-co-alarm/overview accessed Apr. 8, 2018.

There is a need for safer, more practical, versatile, efficient and effective systems for monitoring various hazards, utilities and events that offer greater functionality, connectivity and control, and can affect the safety and integrity of residences and their owners, as well as provide independent third party verification of such information, and other important commercial functions.

SUMMARY OF THE INVENTION

The present invention provides methods and systems for the remote monitoring and recording of historical records of multiple functions and/or utilities in a household or business establishment. Utilities and other factors that can be monitored include seismic activity, moisture or water levels, electricity, gas utilities, such as methane and propane systems and water; hazards, such as detection of smoke, carbon monoxide, radon, dust and mold, conditions such as humidity. Other conditions that can be monitored, recorded and/or controlled include, but are not limited to temperature, noise level or audio, natural gas, methane, radon and geolocation In certain embodiments, the present invention provides systems and methods for remote monitoring and recording of historical records of multiple functions and/or utilities in a household or business establishment. The system may comprise (a) monitoring means for monitoring and/or measuring one or more monitored parameter selected from the group consisting of seismic activity, levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; (b) recording means for maintaining historical records of said monitored parameters over a preselected period of time; and (c) storing means for securely and unalterably maintaining and accessing the historical records of said monitored parameters over said preselected period of time. As used in the present invention, the term "parameter" includes a particular level, or range or of levels, that is monitored and/or recorded by the present system, including, but not limited to, any of the functions and/or utilities mentioned above.

In certain other embodiments, the present invention provides systems and methods for remote monitoring and alerting as to the occurrence of one or more events, said system comprising (a) monitoring means for monitoring one or more monitored parameter selected from the group consisting of levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; (b) recording means for maintaining historical records of said monitored parameters over a preselected period of time; and (c) alerting means for sending out an alert message to one or more remote locations. The alerting means may be pre-programmed to contact one or more persons or locations via email, text message automated phone message or other means of communication upon occurrence of one or more events detected by monitoring means. As used in the present invention, the term "event" includes a change in one or more of the parameters that are listed above and/or other parameters that are monitored by a system of the present invention.

In certain other embodiments, the present invention provides systems and methods for remote monitoring and recording of historical records of multiple functions and utilities in a household or business establishment, alerting as to the occurrence of one or more events, and for remotely responding to such occurrences, said system comprising (a) monitoring means for monitoring one or more monitored parameter selected from the group consisting of seismic activity, levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; (b) recording means for maintaining historical records of said monitored parameters over a preselected period of time; (c) alerting means for sending out an alert message to one or more remote locations; and (d) remote response means by which an operator at said one or more remote locations can override said automated response means.

In certain other embodiments, the present invention provides systems and methods for remote monitoring and recording of historical records of multiple functions and utilities in a household or business establishment, and for providing an automated response to variance of the parameter, said system comprising (a) monitoring means for monitoring one or more monitored parameter selected from the group consisting of seismic activity, levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; (b) recording means for maintaining historical records of said monitored parameters over a preselected period of time; and (c) automated response means for taking a preset action when the monitored parameter is outside a present range surrounding said preset desired level.

In certain other embodiments, the present invention provides systems and methods for remote monitoring and recording of historical records of multiple functions and utilities in a household or business establishment, said system comprising (a) monitoring means for monitoring one or more monitored parameter selected from the group consisting of levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; (b) recording means for maintaining historical records of said monitored parameters over a preselected period of time; (c) alerting means for sending out an alert message to one or more remote locations; (d) automated response means for taking a preset action when the monitored parameter is outside a present range surrounding said preset desired level; and (e) remote response means by which an operator at said one or more remote locations can override said automated response means.

In certain embodiments, the present invention provides systems and methods for providing access to the results of monitoring multiple functions and/or utilities in one or more households and/or business establishments; and/or access to the recorded results [i.e., historical records, whether in electronic form or other hard copy form] of such monitoring. The recorded results may include, for example, a record of when and how often an event occurs, the timing and identification of alerts that are generated and received, and the nature and source of any response, whether generated automatically through preprogramming of the system, or remotely, through a manually implemented response, including override of the system. Such records are useful in generating data, for example, for businesses and home owners, for property management businesses, insurance companies and for first responders for forensic analysis of one or more events or problems at one or more locations, as well as in planning and improving systems and logistics. Such records are also useful in evaluating the management, security status and value of properties in transacting business involving homes, businesses and or multi-property portfolios that include a number of homes, businesses and/or units that can be used for residential and other purposes.

DETAILED DESCRIPTION OF THE INVENTION

Figure 1:
FIG. 1 illustrates a wide variety of monitoring functions that can be accomplished using the system of the present invention.
Figure 2:
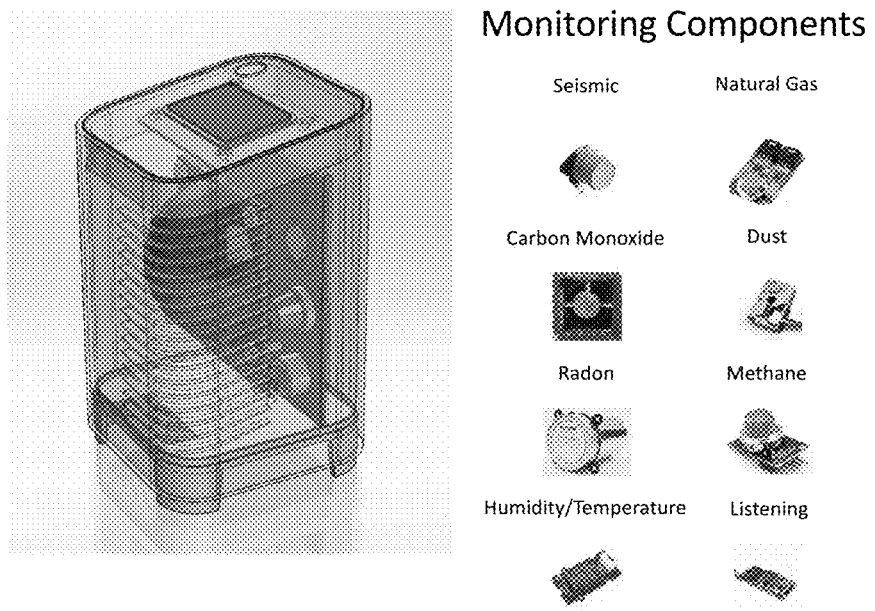
FIG. 2 illustrates components useful as means for monitoring and measurement of the that can be used for the monitoring and measurement of various parameters and functions of possible interest.
Figure 3:
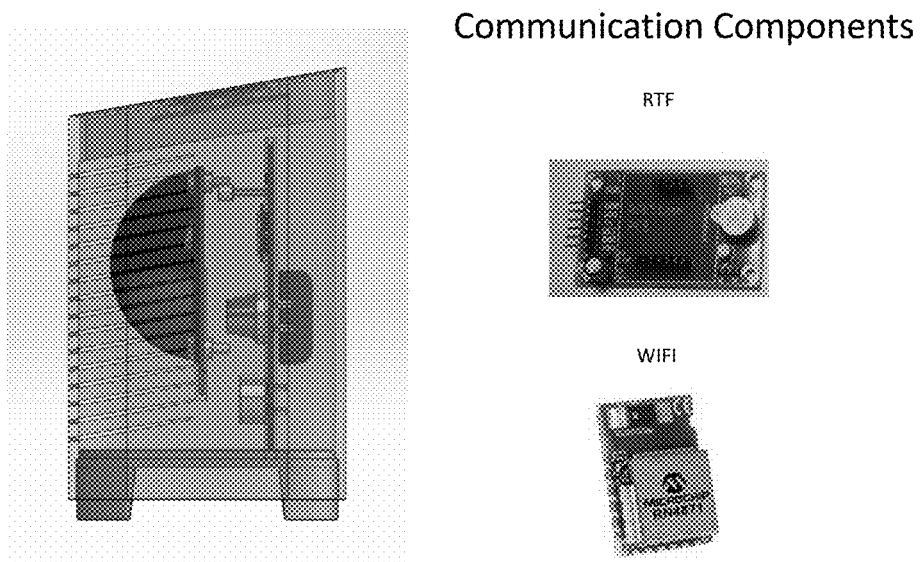
FIG. 3 illustrates components useful as means for communication, or for transmitting a signal, by which the systems of the present invention can communicate with one or more systems to initiate a response to the signal, or for an alert to one or more remote systems or persons.
Figure 4:
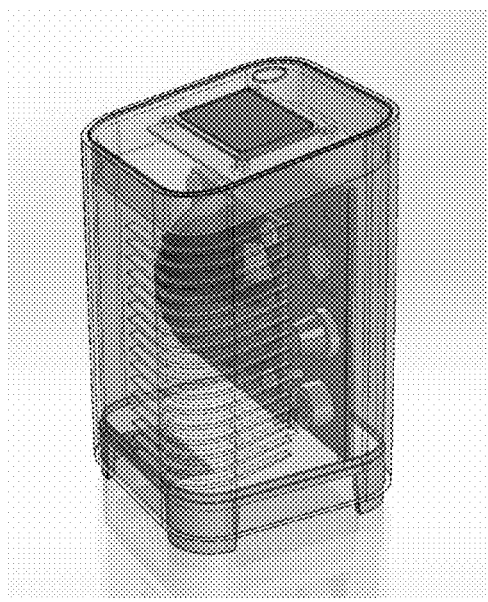
FIG. 4 illustrates components useful as means for providing power and control circuitry that are useful in the systems of the present invention.
Figure 4:
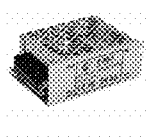
Figure 4:
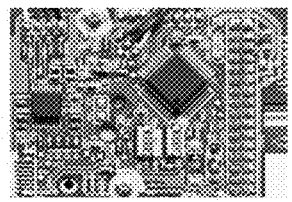
Figure 4:
Figure 4:
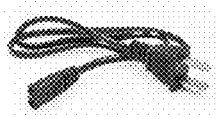
Figure 5:
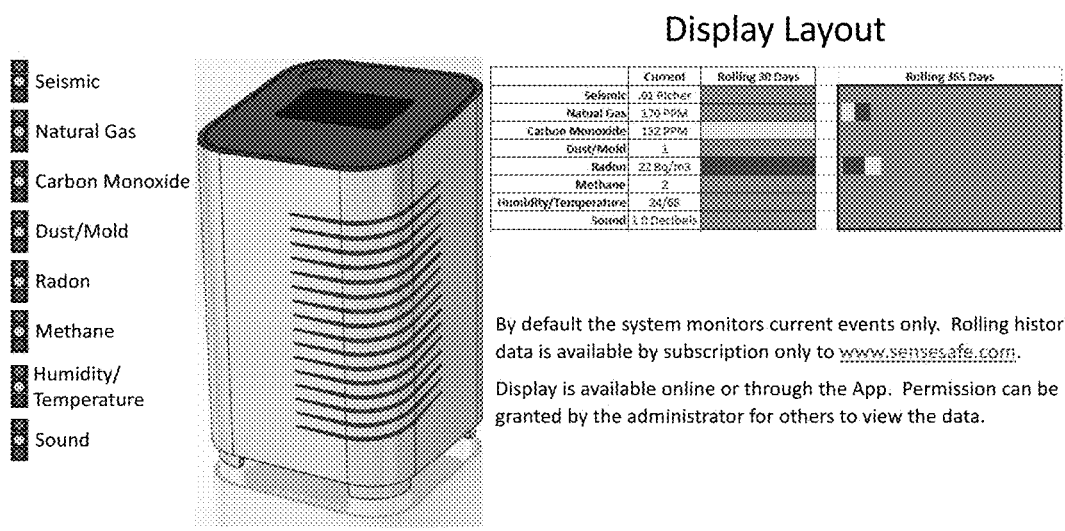
FIG. 5 illustrates a display layout that may be used in the systems of the present invention for visualization of data that is collected and transmitted.
Figure 6:
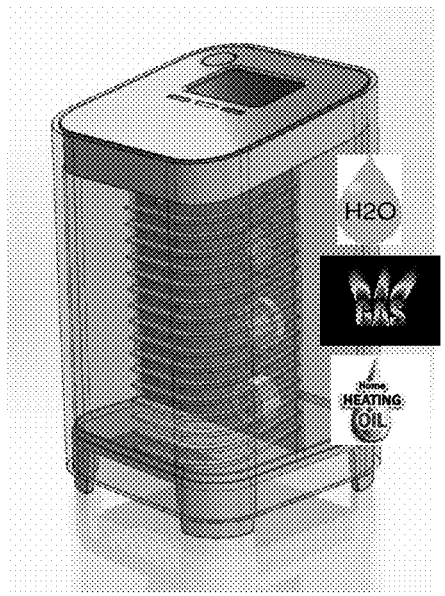
FIG. 6 illustrates additional optional components that may be used in the systems of the present invention to provide additional functionality.

The present invention provides methods and systems for remote monitoring and recording of historical records of multiple functions and utilities in a household or business establishment. Utilities and other factors that can be monitored include seismic activity, gas utilities, such as methane and propane systems and water utilities, hazards, such as detection of smoke, carbon monoxide, radon, dust and mold, and conditions such as humidity, flooding, high and low temperatures, sound and motion. The systems of the present invention can be preset with automated response actions to be conducted as a result of certain events or changes in parameters being detected. For example, the electric and/or gas utility supply can be programmed to shut down if smoke is detected, indicating the possible presence of a fire, or the water supply can be programmed to shut off if the temperature drops below freezing temperature. As another example, supply of all utilities, including electric, gas, and water supply can be programmed to automatically shut down, and a manager and/or the police contacted in the event that a potentially significant change in a monitored parameter, such as noise levels or seismic activity above a predetermined level is detected in a residence or business establishment that is supposed to be unoccupied. As a third example, if a high level of methane is detected, indicating that a leak in the methane system may be present, the supply of methane to the residence or business establishment may be automatically shut off in response. As used herein, the term "monitoring" includes both active and passive camera, audio or other means of observing and/or recording events and/or conditions at a site, as well as the ability to observe and/or review such events and/or conditions, or a historical record of such events and/or conditions, from a remote location.

A remote user, such as a home owner or business manager, may manually control the system using a remote control device or program, which may be programmed into a home or laptop computer, or onto a personal device, such as a cell phone, tablet or other accessory, and which can be downloaded via an application and run on such remote control device. For example, if a residential system is programmed to shut off all utilities upon detection a potentially significant change in a monitored parameter, the system can be set to send out an alert to the remote user. The alert can be in the form of an email, a telephone call, and/or an electronic text message, siren blast, or other preferred means, and can take several forms simultaneously or in series. The system can also be set to send out additional alerts to third parties, such as first responders (e.g., local fire and/or police departments). Upon receiving an alert of an occurrence, the remote user may verify the safety and integrity of the residence, for example by checking for cessation of seismic activity in the area, video monitoring and/or personal inspection, for example by a local official or first responder, and confirmation of the conditions at the residence or business establishment.

Once the safety and integrity of the residence or business facility is confirmed, the remote user may manually override the automated response, or reset the system, turning on all utilities, and/or restoring the preset monitoring conditions.

The present invention further provides methods and systems for establishing and maintaining historical records of the conditions present at a residence or business establishments over an extended period of time. For example, the present invention can provide accurate verification that no radon gas, carbon monoxide, or other hazards have been detected over periods of monitoring that may extend for weeks, months, years, or even decades. Such historical records, maintained with integrity and accuracy, provide a useful verification system that can be relied upon by a user, such as a prospective buyer or agent, and can help establish a fair market value for such residence or business establishment.

Measurement(s) of one or more parameters may be taken at regular intervals as often as desired, for example, may be taken every few seconds, thirty seconds, every minute, ten minutes, fifteen minutes; half hour, hour, two hours; or a longer interval, and the interval may be preset and/or controlled from a remote location by programming means. Thus, in certain embodiments, the present invention provides means for monitoring and/or recording one or more parameters, including seismic activity, natural gas or propane levels, carbon monoxide levels, radon levels, dust and/or mold levels, humidity, temperature, noise levels, smoke, water pressure, water volume and chemical/mineral content of water. The records may be established on a historical basis, or on a rolling basis. For example, in certain embodiments, the present invention provides a secure, permanent and unalterable record of such measurements over a period of time extending for at least one month, at least three months, at least six months, at least nine months, at least 12 months, at least 15 months, at least 18 months, at least 24 months, at least 30 months, at least 36 months, at least four years, at least five years, at least seven years, or at least 10 years. In certain embodiments, access to such secure, permanent and unalterable records may be provided on demand, on a subscription basis, or provided only with the authorization of the record owner through a unique password or authorization code. The records may be maintained on-site and/or via remote storage, for example, by transmission by cellular signal, over the internet or wi-fi connection.

In certain embodiments, the present invention comprises a system for providing a user with access historical records of multiple functions and utilities in a household or business establishment, said system comprising
 a) monitoring means for monitoring one or more monitored parameter selected from the group consisting of levels and usage of utilities, such as oil, gas, and water; smoke levels, carbon monoxide levels, radon levels, dust and mold levels, and conditions such as humidity, flooding, high and low temperatures, sound and motion; and comparing said monitored parameter against a preset desired level; and
 b) recording means for maintaining historical records of said monitored parameters over a preselected period of time;
 c) storing means for securely and unalterably maintaining and accessing the historical records of said monitored parameters over said preselected period of time; and
 d) accessing means for providing access to the stored historical records of step (c), wherein such accessing means is selected from the group consisting of providing said user with a unique password or authorization code that is recognized by the system.

In certain embodiments, the present invention provides means for notifying the record owner, or the record owner's designated recipient, when an event is detected, such as seismic activity, a fire, or other specified events, such as a sudden or unusual change in one or more of the above parameters. The present invention may further provide means for immediately notifying first responders, such as local police, fire and/or other services, when such an event is detected. The means for notification may be in any appropriate form, including, but not limited to, an alert via a cell phone, computer and or other remote device; telephone notification to a business and/or residence; and/or alert to a security representative, police department, fire department, and/or additional designated responders.

In certain embodiments, the present invention provides a system by which two or more monitoring devices of the present invention, located at two or more residential and/or business units is networked, so that the two or more monitoring devices can be viewed, monitored, and/or accessed, and can receive notifications, through a single channel or device, such as a cell phone, computer or other remote device. For example, a business that manages multiple units at a single [e.g., multi-unit] property, or that manages multiple properties at different locations, may set up a single web-site or program on a computer or smart-phone as a point for viewing, monitoring or accessing information regarding multiple units and/or multiple properties. In such embodiments, each unit and/or each property location is preferably assigned an individual identifying name or other identifier. Additionally, the system can be programmed so that two or more monitoring devices located at a single property, or located at two or more properties at different locations, provide notifications through a single channel to one or to multiple remote devices. In certain embodiments, the notification is set up in parallel, so that the notification goes to multiple remote devices simultaneously. Alternatively, the notification is set up to run in series, first sending notification to one remote device; and subsequently to one or more additional remote devices. In series, the monitoring device of the invention can be set up to first send notification to one remote device ['user A']. If user A does not respond within a pre-set period of time for response, a subsequent notification is then automatically sent to one or more follow-up remote devices in series ['user B', 'user C' and so on].

In certain embodiments, the present invention further provides means for identifying the location of the event or alert, i.e., means for geolocation, such as through generation of identifying geographic coordinates utilizing real-time locating systems (RTLS), and standards such as those of the International Organization for Standardization (ISO) or Natural Area Code (NAC); a global position system ("GPS") radar. The means for geolocation provides parties, such as the owner, manager, and/or first responders, with immediate and accurate information as to the location of the event or the business and/or residence, that is, the source of the alert or notification, and the most expedient route for getting to the location of the source. The means for geolocation may comprise an integral component of the system of the present invention, and may be connected in such a manner such that prevents removal of the geolocation means from the system. The system of the present invention may also provide a unique identification means, for example, matching the particular monitoring system, and the historical data associated with that system, to a particular device and/or location, to prevent tampering or fraud, such that movement or removal of the system results in the invalidation of the unique identification means, and monitoring means and historical data associated with such means becomes identified as potentially being invalidated.

In certain embodiments, the present invention provides means for automatically responding to the detection of a specified event, such as automatically shutting off the water, gas and/or other utility supply, to a residence or business establishment, upon detecting a potentially significant change in a monitored parameter, such as smoke indicating the presence of a fire, and/or extreme cold and/or hot temperatures. In certain embodiments, the present invention further provides means for remotely controlling one or more functions in a residence or business establishment. For example, the owner or responder may, using remote means, which may be operated via an application and run on a remote control device, such as a cell phone, a home, laptop or automobile computer, or a remote control accessory designed for use with the present invention. For example, through such remote means, the owner or responder may cut off one or more functions in the residence or business establishment, or may turn on one or more functions in the residence or business establishment. For example, after being alerted to the presence of smoke in a residence, the owner or responder may remotely turn off the gas, oil, and/or other utility supply to the residence or business establishment. Once satisfied that the risk of fire has been foreclosed, the owner or responder may remotely restore the functions to their normal operation, e.g., by turning the gas, oil and/or other utility supply back on. The owner/responder may also utilize video and/or audio surveillance in order to confirm conditions at the premises, and initiate appropriate action in response. For example, the owner/responder may send out alerts to one or more individuals to respond to an event, or may temporarily turn on the sprinkler system in a designated area where flames are observed. Such responses may include, for example, overriding the automatic system response in order to restore default settings.

The present invention also provides means for data compilation, transformation and storage. Through use of the sensors, the system of the invention detects and transmits real-time data which can be compiled, transformed and stored for multiple uses, including provision of historical data and trends. The system can be used to provide accurate data, which can further be certified through verification means that will authenticate the geographical location and origin of each data point that is uploaded. If the system is moved, it will reference the break in geographic continuity in the data set. Use of such data has wide applications for homeowners, homebuyers, apartment building occupants, and for internet-based businesses, such as short-term stay housing, such as provided by the internet sites VRBO and Airbnb.

The present invention can be used for a wide range of sites, such as single home or multiple unit residences; industrial plants, office buildings, warehouses and other commercial facilities. In a modified form, the present invention can also be installed in a mobile unit, such as a car, a cell phone, or an appliance, which can be monitored for continued function as well as for tracking its location.

Monitoring Components

The present invention includes means for monitoring or measuring a number of parameters or functions. Such means for monitoring or measuring may further comprise or be functionally connected with means for recording historical data, such that the parameter or function that is monitored or measured can be archived for a period of time and provide a record of said parameter or function over an extended period of time. Such means for monitoring or measuring may also further comprise or be functionally connected with means for transmission of a signal, such as an alert, a text or telephone call, such that the owner/occupant, business proprietor, manager or responsible agent, and/or designated persons, including first responders such as a fire department, police department, or other service provider that is to be alerted or notified when the monitoring or measuring means detects a preselected event, or change in one or more of the parameters or functions being monitored. The means of monitoring, or means of transmission of a signal may further comprise, or be functionally connected with, a means for effecting a particular change to a system or parameter, such that one or more system the residence or business will respond, or a change in one or more systems are programmed to occur in response to detection of a preselected event occurrence, or a change in one or more of the parameters or functions being measured. For example, the flow of one or more utilities, such as gas or water, may be shut off in response to the detection of a potentially significant change in a monitored parameter above or below a preselected threshold level.

Thus, the present invention comprises one or more of the following elements that useful for the monitoring or measurement of the parameters or functions that are desired to be monitored or measured.

Seismic Activity Monitors:

Means for monitoring seismic activity that are useful in the invention include, for example, the SM-24 geophone element (Input/Output Inc., Stafford Tex.). Said means for monitoring seismic activity may further comprise or be connected to means for recording, so that the seismic activity may be monitored and recorded historically. Said means for monitoring seismic activity may also be connected to means for notification, that will provide automated alerts, as programmed, to the occupant/owner; manager or responsible agent; and/or to first responders such as fire, police, or other service providers.

Natural Gas/Propane Monitors:

Means for monitoring natural gas or propane that are useful in the invention include sensors, for example, the LPG Gas Sensor—MQ-6 (Winsen Electronic Technology Co., Ltd, Zhengzhou China) which is suitable for sensing liquefied petroleum gas, propane and butane, at gas concentrations from 200 to 10,000 ppm. Said means for monitoring natural gas or propane may further comprise or be connected to means for recording, so that the natural gas or propane concentration may be monitored and recorded historically. Said means for monitoring natural gas or propane may also be connected to means for notification, that will provide automated alerts, as programmed, to the occupant/owner; manager or responsible agent; and/or to first responders such as fire, police, or other service providers.

Carbon Monoxide Monitors:

Means for monitoring carbon monoxide that are useful in the invention include sensors, for example, the Carbon Monoxide Sensor—MQ-7 (Winsen Electronic Technology Co., Ltd, Zhengzhou China) which is suitable for sensing CO-gas concentrations from 20 to 2,000 ppm. Said means for monitoring carbon monoxide may further comprise or be connected to means for recording, so that the carbon monoxide concentration may be monitored and recorded historically. Said means for monitoring carbon monoxide may also be connected to means for notification, that will provide automated alerts, as programmed, to the occupant/owner; manager or responsible agent; and/or to first responders such as fire, police, or other service providers.

Dust Monitors:

Means for monitoring dust levels that are useful in the invention include sensors, for example, the Optical Dust Sensor—GP2Y1010AU0F (Sharp Corporation, HiSense-USA Corporation, Suwanee, Ga.). This optical dust sensor can be powered up to 7V DC. The output of the sensor is an analog voltage proportional to the measured dust density, with a sensitivity of 0.5V/0.1 mg/m3. Said means for dust monitoring may further comprise or be connected to means for recording, so that the dust concentration may be monitored and recorded historically. Said means for monitoring concentration of optical dust may also be connected to means for notification, that will provide automated alerts, as programmed, to the occupant/owner; manager or responsible agent; and/or to first responders such as fire, police, or other service providers.

Mold Monitors:

Means for monitoring mold levels that are useful in the invention include sensors, for example, the Dylos DC 1100 Pro Air Purifier Test Monitor (Dylos Corporation, Riverside Calif.) may be adapted for use as an integrated element of the present invention. This mold monitor screens for small and large particle counts present in the air, and is sensitive for particles from 0.5 to 2.5 microns. The monitor can be programmed for readings every six seconds, and Said means for dust monitoring may further comprise or be connected to means for recording, so that the dust concentration may be monitored and recorded historically. Said means for monitoring concentration of optical dust may also be connected to means for notification, that will provide automated alerts, as programmed, to the occupant/owner; manager or responsible agent; and/or to first responders such as fire, police, or other service providers.

Radon Monitors:

Means for monitoring radon levels that are useful in the invention include sensors, for example, the Radon SS Gas Sensor—1750 pCi/l Rn (Euro-Gas Management Services, Devon, UK). This radon sensor has a standard range of 1750 pCi/l Rn. It has a field range of 0-65K Bq/m3 and resolution of 1 Bq/m3. Said means for monitoring radon may further comprise or be connected to means for recording, so that the dust concentration may be monitored and recorded historically. Said means for monitoring radon may also be connected to means for notification, that will provide automated alerts, as programmed, to the occupant/owner; manager or responsible agent; and/or to first responders such as fire, police, or other service providers.

Humidity/Temperature Sensors:

Means for monitoring humidity that are useful in the invention include sensors, for example, the Humidity and Temperature Sensor—RHT03/DHT-022 (MaxDetect Technology Co., Ltd. Shenzhen, CN). This humidity/temperature sensor has an operating range of 0-100% humidity, and −40°-80° Celsius. Said means for monitoring humidity and temperature may further comprise or be connected to means for recording, so that the humidity and temperature conditions may be monitored and recorded historically. Said means for monitoring humidity and temperature may also be connected to means for notification, that will provide automated alerts, as programmed, to the occupant/owner; manager or responsible agent; and/or to first responders such as fire, police, or other service providers.

Additional parameters that may be monitored, recorded and/or transmitted include video or camera surveillance, audio or sound surveillance (for example, condenser microphones to listen for the sound of running water), water pressure and volume, and mineral or chemical content of water.

Communication Components

The present invention also includes means for transmission of a signal to one or more designated locations, which may be useful to alert the occupant/owner; manager or responsible agent; and/or first responders such as fire, police, or other service providers, that a pre-specified event has occurred. The means for transmission of a signal may be by any means, including radio transmission frequency or RTF, or via Wi-Fi module. Means for transmission of a signal that are useful in the invention include, for example, the ESP8266 WiFi Module (SparkFun Electronics, Niwot, Colo.), which provides system-ready WiFi networking functions that can be accessed by microcontrollers, and integrated with sensors and other application-specific devices that are used in the invention.

Power & Microcontroller Circuit Components

The present invention also includes standard components required for power supply and circuitry, including power cord, battery backup and a control module. The control module useful for the present invention, may be a microcontroller, for example, a programmable system-on-chip circuit board, such as the FreeSOC3 Development Board—PSoC® 5LP (Cypress Semiconductor Corporation, San Jose Calif.), which provides for highly adaptable integration of multiple digital and analog peripheral functions. The system of the present invention can be run by any standard primary power source. In certain preferred embodiments, the system will run on electrical power available on-site as the primary power source. The system of the present invention preferably includes at least one back-up power source, such as a battery. The battery preferably can hold a sufficient charge to run the system for at least one hour, preferably two, three, four, six, eight or more hours, and should be continuously maintained at full charge by the primary power source so long as it is running.

Optional Functionality

In certain embodiments, the present invention will include additional elements as means for enabling one or more optional functionalities of the invention. The skilled practitioner will recognize that such elements are readily available for integration and use with the present invention. For example, if it is desired that the system of the invention includes the functionality of controlling, disabling or shutting off a fluid supply, such as water or oil supply, the invention will further comprise means for controlling fluid flow in a system via transmission of a signal from a computer microcontroller. For example, the 12V Solenoid Valve—¾" (Aqua Tech Trading Corporation Ltd, Chongqing, CN) is a controlled fluid valve which is connected to a fluid source, after which it will interrupt the flow until 12V is applied to the fast-on connectors on the solenoid. The 12V Solenoid Valve—¾" operates at a minimum of 3 PSI, allowing around 3 liters/minute of flow.

In certain embodiments, by default, the system monitors current events only. In such embodiments, rolling historical data is available by subscription only, for example, by access to approved control websites. Access can be granted through permission from a control website. The system can certify the accuracy of the data by authenticating its geographic location and time each time the data is uploaded. If the system is moved from one address to another, the change in location will be referenced as a break in the data set. The system will also record any time that data is accessed and/or uploaded and report any irregular activity that might compromise the integrity of the recorded historical data.

Display of data may be available online or through a smartphone app, which can be downloaded via the internet. Permission can be granted by the administrator for others to view the data.

While the invention has been described with respect to certain embodiments, it is contemplated numerous modifications and additions are possible without varying from the essential scope of the invention as described and claimed. The skilled practitioner will recognize that such modifications and additions constitute a part of the present invention.

All publications and source materials, such as the specific components specified for use in the commercial embodiment, described herein are hereby incorporated by reference, as if fully reproduced herein. The suppliers' and manufacturers' websites were accessed on Apr. 20, 2018.

The invention claimed is:

1. A stand-alone portable device for remotely generating and maintaining an unalterable authenticated historical record, said unalterable authenticated historical record comprising historical monitoring data and historical geolocation data, said historical monitoring data comprising measurements of one or more parameters over a period of time, and said historical geolocation data authenticating the geographic location of each data point of said historical monitoring data over said period of time, said device comprising:
- one or more monitors for generating historical monitored data comprising measurements of one or more parameters over a period of time, wherein said one or more monitors are selected from the group consisting of a seismic activity monitor, a natural gas or propane sensor, a carbon monoxide sensor, a dust sensor, a mold monitor, a radon sensor, a humidity and temperature sensor, and an audio monitor,
- a global positioning system (GPS) or Real-Time Locating System (RTLS) for generating historical geolocation data, wherein said historical geolocation data is generated over the same period of time as said historical monitored data,
- a transmitter for transmitting a signal, said signal comprising said historical monitoring data and said historical geolocation data generated over said period of time, wherein said historical monitoring data and said historical geolocation data generated over said period of time are associated to generate an unalterable authenticated historical record of said historical monitoring data at said geographic location over said period of time, wherein said transmitter is selected from the group consisting of a cellular signal transmitter, a radio transmission frequency transmitter, and a wi-fi transmitter module, and a power source.

2. The device of claim 1, wherein the power source is selected from the group consisting of an electrical cord and a battery.

3. The device of claim 2, further comprising at least one back-up power source.

4. The device of claim 1, further comprising storage means for securely maintaining said unalterable authenticated historical record of said multiple historical monitoring data at said geographic location over said period of time.

5. The device of claim 1, further comprising one or more monitors for monitoring levels and usage of one or more utilities selected from the group consisting of: oil, gas, and water.

6. The device of claim 4, wherein said storage means is located at a remote location.

7. A system for generating, maintaining and accessing an authenticated historical record of historical monitoring data at a given geographic location, said system comprising:
- a stand-alone portable device for remotely generating and maintaining an unalterable authenticated historical record, said unalterable authenticated historical record comprising historical monitoring data and historical geolocation data, said historical monitoring data comprising measurements of one or more parameters over a period of time, and said historical geolocation data authenticating the geographic location of each data point of said historical monitoring data over said period of time, said device comprising:
- one or more monitors for generating historical monitored data comprising measurements of one or more parameters over a period of time, wherein said one or more monitors are selected from the group consisting of a seismic activity monitor, a natural gas or propane sensor, a carbon monoxide sensor, a dust sensor, a mold monitor, a radon sensor, a humidity and temperature sensor, and an audio monitor,
- a global positioning system (GPS) or Real-Time Locating System (RTLS) for generating historical geolocation data, wherein said historical geolocation data is generated over the same period of time as said historical monitored data, a transmitter for transmitting a signal, said signal comprising said historical monitoring data and said historical geolocation data generated over said period of time, wherein said historical monitoring data and said historical geolocation data generated over said period of time are associated to generate an unalterable authenticated historical record of said historical monitoring data at said geographic location over said period of time, wherein said transmitter is selected from the group consisting of a cellular signal transmitter, a radio transmission frequency transmitter, and a wi-fi transmitter module,
- a power source, and
- one or more remote devices for accessing said authenticated historical record, said one or more remote devices being capable of receiving the signal transmitted by said device; wherein said one or more remote devices are selected from the group consisting of a cell-phone, tablet, or computer.

8. The system of claim 7, wherein a user of said one or more remote devices can access said authenticated historical record after providing a unique password or authorization code that is recognized by the system.

* * * * *